(12) United States Patent
Amhof et al.

(10) Patent No.: US 6,238,623 B1
(45) Date of Patent: May 29, 2001

(54) LABELS AND TRACKING SYSTEMS FOR STERILIZATION PROCEDURES

(75) Inventors: Anita Amhof; Urs Jauslin, both of Rueschlikon (CH); Ramon T. Ignacio, Flemington, NJ (US); Florian Weinig; Christian Stoop, both of Rueschlikon (CH)

(73) Assignee: 3M Innovative Properties Company, Saint Paul, MN (US)

( * ) Notice: Subject to any disclaimer, the term of this patent is extended or adjusted under 35 U.S.C. 154(b) by 0 days.

(21) Appl. No.: 09/019,445

(22) Filed: Feb. 5, 1998

Related U.S. Application Data

(63) Continuation-in-part of application No. 08/859,759, filed on May 21, 1997, now Pat. No. 6,063,631.

(51) Int. Cl.$^7$ ........................................................ A61L 2/28

(52) U.S. Cl. .............................. 422/58; 422/56; 422/57; 428/42.3; 428/41.8; 428/42.1; 116/206

(58) Field of Search .................................. 116/206, 207, 116/216; 422/56, 58, 57; 428/41.8, 42.1, 42.2; 40/638, 630, 299.01

(56) References Cited

U.S. PATENT DOCUMENTS

| | | |
|---|---|---|
| 3,183,173 | 5/1965 | Oakes . |
| 3,568,627 | 3/1971 | Selinger . |
| 3,627,469 | 12/1971 | Cheng . |

(List continued on next page.)

FOREIGN PATENT DOCUMENTS

| | | |
|---|---|---|
| 2 027 604 | 5/1970 | (DE) . |
| 268 396 A1 | 5/1989 | (DE) . |
| 273 775 A1 | 11/1989 | (DE) . |
| 273 776 A1 | 11/1989 | (DE) . |
| 90 04 818 | 4/1990 | (DE) . |
| 90 04 818 U | 7/1990 | (DE) . |
| 195 09 505C1 | 1/1996 | (DE) . |
| 0 014 447 A1 | 8/1980 | (EP) . |
| 0 069 037 A1 | 1/1983 | (EP) . |
| 0 421 760 B1 | 3/1994 | (EP) . |
| 0 630 820 | 12/1994 | (EP) . |
| 0 707 186 A1 | 4/1996 | (EP) . |
| 914833 | 5/1999 | (EP) . |
| 0 914 833 A2 | 5/1999 | (EP) . |
| 49-46440 | 12/1974 | (JP) . |
| WO 93/16386 | 8/1993 | (WO) . |
| WO 96/33242 | 10/1996 | (WO) . |
| WO 98/46994 | 10/1998 | (WO) . |

OTHER PUBLICATIONS

Derwent Publications Ltd., JP 49 046440 B, Dec. 10, 1974 (Abstract).
Steris Process Monitoring, 6122025 Rev. C, May 1995.
Advertisements for Sterrard* Chemical Indicator Strip, Advanced Sterilization Products, 1995.
Borneff et al., "On the Efficacy and Validation of $H_2O_2$ Plasma Sterilizers".
P. Mecke, "Hydrogen Peroxide Plasma—an Interesting Microbial Concept", Hygiene+ Medizin, 1992: 17:537–543.
Eskenazi et al., "Evaluation of Glutaraldehyde and Hydrogen Peroxide for Sanitizing Packaging Materials of Medical Devices in Sterility Testing", J. Assoc. Off. Anal. Chem. (vol. 65, No. 5) 1982.

(List continued on next page.)

*Primary Examiner*—Deborah Jones
*Assistant Examiner*—Jennifer McNeil
(74) *Attorney, Agent, or Firm*—John A. Burtis

(57) ABSTRACT

A novel label may be used in a novel sterilization tracking system. The label preferably has first and second portions and a first and second liners. Perforations may preferably attach the first portion to the second portion. The label is particularly suitable for use in monitoring and/or tracking hydrogen peroxide sterilization procedures.

13 Claims, 3 Drawing Sheets

U.S. PATENT DOCUMENTS

| | | |
|---|---|---|
| 3,627,698 | 12/1971 | Rey et al. . |
| 3,654,179 | 4/1972 | Bauer . |
| 3,654,180 | 4/1972 | Bauer . |
| 3,667,916 | 6/1972 | Sliva et al. . |
| 3,704,096 | 11/1972 | Verses et al. . |
| 3,862,824 | 1/1975 | Chapman . |
| 3,899,295 | 8/1975 | Halpern . |
| 4,042,336 | 8/1977 | Larsson . |
| 4,091,921 | 5/1978 | Lewis . |
| 4,098,577 | 7/1978 | Halpern . |
| 4,138,216 | 2/1979 | Larsson et al. . |
| 4,145,186 | 3/1979 | Anderson . |
| 4,155,895 | 5/1979 | Rohowetz et al. . |
| 4,165,399 | 8/1979 | Germonprez . |
| 4,166,044 | 8/1979 | Germonprez et al. . |
| 4,168,779 | 9/1979 | Yokokoji et al. . |
| 4,169,124 | 9/1979 | Forstrom et al. . |
| 4,179,397 | 12/1979 | Rohowetz et al. . |
| 4,188,437 | 2/1980 | Rohowetz . |
| 4,194,622 | 3/1980 | Lewis . |
| 4,206,844 | 6/1980 | Thukamoto et al. . |
| 4,240,926 | 12/1980 | McNeely . |
| 4,328,182 | 5/1982 | Blake . |
| 4,407,960 | 10/1983 | Tratnyek . |
| 4,416,984 | 11/1983 | Wheeler, Jr. . |
| 4,448,548 | 5/1984 | Foley . |
| 4,521,376 | 6/1985 | Witonsky et al. . |
| 4,579,823 | 4/1986 | Ryder . |
| 4,643,876 | 2/1987 | Jacobs et al. . |
| 4,696,843 | * 9/1987 | Schmidt . |
| 4,717,661 | 1/1988 | McCormick et al. . |
| 4,741,437 | 5/1988 | Gorski et al. . |
| 4,756,758 | 7/1988 | Lent et al. . |
| 4,756,882 | 7/1988 | Jacobs et al. . |
| 4,885,253 | 12/1989 | Kralovic . |
| 4,898,762 | 2/1990 | Brown et al. . |
| 4,935,371 | 6/1990 | Rickloff . |
| 4,968,351 | 11/1990 | Ahmed et al. . |
| 5,045,283 | 9/1991 | Patel . |
| 5,048,870 | 9/1991 | Mangini et al. . |
| 5,053,339 | 10/1991 | Patel . |
| 5,073,488 | 12/1991 | Matner et al. . |
| 5,084,239 | 1/1992 | Moulton et al. . |
| 5,087,659 | 2/1992 | Fujisawa . |
| 5,139,957 | 8/1992 | Grack . |
| 5,167,923 | 12/1992 | Van Iperen . |
| 5,254,473 | 10/1993 | Patel . |
| 5,260,023 | 11/1993 | Evans, II . |
| 5,316,575 | 5/1994 | Lent et al. . |
| 5,329,713 | 7/1994 | Lundell . |
| 5,344,017 | 9/1994 | Wittrock . |
| 5,352,155 | 10/1994 | Fahey . |
| 5,377,496 | 1/1995 | Otto et al. . |
| 5,380,045 | 1/1995 | Comann . |
| 5,393,100 | 2/1995 | Coe . |
| 5,451,372 | 9/1995 | Larsson et al. . |
| 5,482,684 | 1/1996 | Martens et al. . |
| 5,498,526 | 3/1996 | Caputo et al. . |
| 5,516,648 | 5/1996 | Malchesky et al. . |
| 5,518,763 | 5/1996 | Patnode et al. . |
| 5,518,927 | 5/1996 | Malchesky et al. . |
| 5,552,320 | 9/1996 | Smith . |
| 5,597,634 | 1/1997 | Bloomer et al. . |
| 5,620,656 | 4/1997 | Wensky et al. . |
| 5,622,764 | 4/1997 | Battles . |
| 5,623,810 | 4/1997 | Dey et al. . |
| 5,667,753 | 9/1997 | Jacobs et al. . |
| 5,709,067 | 1/1998 | Dey et al. . |
| 5,732,529 | 3/1998 | Dey et al. . |
| 5,882,611 | 3/1999 | Williams et al. . |
| 5,887,716 | 3/1999 | Williams et al. . |
| 5,942,438 | 8/1999 | Antonoplos et al. . |
| 5,955,025 | 9/1999 | Barrett . |
| 5,990,199 | * 11/1999 | Bealing et al. . |

OTHER PUBLICATIONS

Steris Process, Chemical Monitoring Strips for Independent Monitoring of the Steris Process, Brochure of Steris Corporation.

VP Papier Stericlin, "Stericlin System for Batch Documentation", Brochure of Vereinigte Papier Waren Fabriken GmbH (Original German and Informal English Translation—17 pages total).

Sterrad Sterilization Indicating Tape 14200 Instructions for Use.

Sterrad Sterilization System Product Brochure.

Steris Process™ Chemical Monitoring Strips 501(k) Summary.

* cited by examiner

LABELS AND TRACKING SYSTEMS FOR STERILIZATION PROCEDURES

CROSS REFERENCE TO RELATED APPLICATION

This application is a continuation-in-part of and claims priority from U.S. patent application Ser. No. 08/859,759 entitled, "Sterilization Indicator" filed May 21, 1997 now U.S. Pat. No. 6,063,631.

FIELD OF INVENTION

This invention relates to tracking systems for sterilization procedures and the like and components such as labels for use in such tracking systems.

BACKGROUND

There are many different types of sterilization procedures available to those who sterilize products. While steam sterilization remains a popular procedure for sterilizing objects, the sterilization art now has many different procedures that provide options for those interested in sterilizing objects. Hydrogen peroxide sterilization procedures offer one option. As used herein, vapor phase, liquid phase and plasma hydrogen peroxide sterilization procedures are all within the broad aegis of hydrogen peroxide sterilization procedures.

The sterilization art recently witnessed the introduction of plasma sterilizers. U.S. Pat. Nos. 4,643,876 and 4,756,882 are said to cover the Sterrad® Hydrogen Peroxide Plasma Sterilizers available from Advanced Sterilization Products of Irvine, Calif. U.S.A. (a division of Johnson and Johnson). U.S. Pat. No. 5,084,239 describes a peracetic acid plasma sterilizer. Peracetic acid plasma sterilizers are sold by AbTox of Mundelein, Ill. Other patents assigned to AbTox include U.S. Pat. Nos. 5,115,166; 5,376,332; 5,413,759; 5,413,760 and 5,472,664.

There is a problem associated with tracking goods treated by a Sterrad® Hydrogen Peroxide Plasma Sterilizer. While chemical indicators and chemical indicating tape are sold for use with Sterrad® sterilizers, there are believed to be no adhesive labels available for use with the Sterrad® sterilizers that include an indicating composition that is responsive to the sterilization process associated with the Sterrad sterilizer. Of course tracking systems for use with the Sterrad sterilizers would not include such adhesive labels.

Dry heat sterilization, formaldehyde, gamma irradiation, ethylene oxide procedures and the above described hydrogen peroxide sterilization procedures provide a daunting array of options for those who sterilize objects. Often a hospital will utilize several different types of sterilizers to address its needs.

The state of objects to be sterilized should be carefully managed and monitored at all times, especially prior to the use of such objects on patients. This holds true for any sterilization procedure. When a hospital utilizes several different types of sterilizers, it makes this problem even more complex.

There are many tracking systems that include steps taken even before the objects emerge from a sterilizer. U.S. Pat. No. 3,568,627 discloses a combined record card and sterilization indicator. The card and indicator are for use in a steam sterilizer.

European Patent Application No. 630 820 discloses a process and system for monitoring material flow during the preparation of sterile goods. That document describes data carriers that contain two sections with identical data sets. One section may be adhesively attached to a treatment protocol, while the other section may remain at the sterilized unit. Printable adhesive labels are also described that include a carrier layer that possesses a first adhesive coating and a data carrier layer that adheres to the carrier layer by means of a second adhesive coating. The adhesive strength of the second adhesive coating toward the carrier layer is said to be lower than the adhesive strength of the first adhesive coating to an adhesive accepting surface of a sterile goods container.

Vereinigte Papierwarenfabriken GmbH of Munich, Germany sells the Stericlin System Batch Documentation. Stericlin systems are available at least in Germany. A first Stericlin system includes a label for use with certain steam sterilization procedures. A second Stericlin system includes a label for use with certain ethylene oxide sterilization procedures. Codes for the objects to be sterilized are utilized. The Stericlin systems are limited as they do not include any labels for use in any sterilization procedures other than the particular steam and ethylene oxide procedures mentioned above. For example, the Stericlin systems do not include any labels with an indicating ink that is suitable for use in a hydrogen peroxide sterilization procedure. The use of an existing Stericlin label in a tracking system for a hydrogen peroxide sterilizer can be misleading or confusing.

The Stericlin systems include an elongate label that has an adhesive coated major left portion and an adhesive coated minor right portion. The left portion is separate from the right portion by virtue of a cut. The left and right portion are located on a liner that includes a single incision extending perpendicular to the direction of elongation of the labels at the middle of the major left portion. As discussed in greater detail below, the right portion of the liner is associated with the entire right portion of the label and about one half of the left portion of the label.

The Stericlin labels for the steam and ethylene oxide procedures also suffer drawbacks. Only the left portions of the labels include an ink that changes color upon exposure to a sterilization procedure. The left portion of the Stericlin label for use in steam sterilization procedures includes a strip of ink which is brown upon exposure to the sterilization procedure. The right portion is free of any indicating ink. The left portion of the Stericlin label for use in ethylene oxide sterilization procedures includes a strip of ink which is yellow upon exposure to the ethylene oxide sterilization procedure. The right portion is free of any indicating ink.

The left portions of the labels are initially placed on the sterile goods packaging with about one half of its adhesive. This is accomplished by leaving one half of the liner on the adhesive of the left portion. A problem exists when the labels are used with sterile goods packaging made of crepe sheet paper. When the labels are used with goods packaging made of crepe sheet paper, the left portion is placed on an opening flap formed through a fold because, during the vacuum portion of the sterilization procedure, the label can become detached from the surface of the package. The Stericlin system even suggests that additional tape could be used to secure the label in an effort to address this problem. The left portions of the labels are thereafter removed from the sterilized goods packaging, the remaining portion of the liner is removed, and the left portions are thereafter placed on patient's files using the other half of their adhesives. This can lead to several problems such as damage to the goods packaging, and partial separation or "flagging" on the patient's file.

The right portions of the labels are placed on batch cards. Because the right portions do not include indicating ink, the information provided by the indicating ink is not available on the batch card.

German Utility Model (Gebrauchsmuster) No. G 90 04 818.0 (assigned to Vereinigte Papierwarenfabriken GmbH) discloses a label for sterile packaging. The label includes a major left portion and a minor right portion separated by a cut. The left portion may have an indicating ink. Indicating inks for water vapor sterilization, ethylene oxide gas sterilization and formaldehyde sterilization are mentioned. The minor right portion of the label is free of any indicating ink. A two part liner is disclosed. The first part covers about one-half of the major left portion, the second part covers the rest of the major left portion and all of the right portion.

SUMMARY OF THE INVENTION

The present invention provides a label for use in a sterilization tracking system. The label securely adheres to the packaging of the goods to be sterilized even during sterilization procedures which utilize a vacuum. The label affords the user complete freedom to mark, stamp or print on the label. A code for the objects to be sterilized is entirely optional and not necessary.

The present invention includes a label preferably comprising first and second portions. Preferably, the second portion is easily, manually separable from the first portion. The first and second portions may be rendered manually separable in a variety of manners such as by scoring, stamping or perforating the boundary between the first and second portions. Although in some embodiments, the present invention may be practiced with a single liner, the label preferably includes a first removable liner removably attached to the first portion and a separate and distinct second liner removably attached to the second portion. The first removable liner is adhered to the adhesive of the first portion and free of attachment to the second portion. The second removable liner is adhered to the adhesive of the second portion and free of attachment to the first portion.

The first portion preferably has a composition thereon that changes indicating state (e.g. color) upon exposure to a sterilization procedure. The second portion also preferably has a composition that changes indicating state (e.g. color) when exposed to a sterilization procedure. Thus, the information provided by the indicating compositions is available to a user viewing either the first or the second portion of the label.

Unlike the Stericlin system which ultimately removes all portions of the label from the packaging of the sterilized goods, the first portion of the label of the present invention may remain with the packaging of the sterilized goods for use in other control procedures.

The label is particularly suitable for use with objects that are to be subjected to a hydrogen peroxide sterilization procedure. The label comprises a first side constructed to receive indicia and a second side having an adhesive associated therewith. A removable liner is adhered to the adhesive. In this embodiment, the label includes an indicating composition with a first indicating state (e.g. a first color) prior to exposure to the hydrogen peroxide sterilization procedure and a second indicating state (e.g. a second color different than the first color) after exposure to the hydrogen peroxide sterilization procedure.

The present invention may also be described as a method of tracking objects to be sterilized which utilizes a novel label as discussed above.

BRIEF DESCRIPTION OF THE DRAWINGS

The present invention will be further described with reference to the accompanying drawing wherein like reference numerals refer to like parts in the several views, and wherein:

FIGS. 4*a* through 4*f* schematically illustrate the use of the label substantially as described in FIG. 3 wherein:

FIG. 4*a* illustrates with solid lines a series of labels on an optional perforated liner, and a label that could be removed from the liner with dashed lines;

FIG. 4*b* illustrates the label that has been removed from the liner of FIG. 4*a;*

FIG. 4*c* illustrates a package of items to be sterilized and the label of FIG. 4*b* adhered to the package by the adhesive exposed when the label was removed form the liner shown in FIG. 4*a;*

FIG. 4*d* illustrates the step of placing the package of objects to be sterilized into a sterilizer;

FIG. 4*e* shows the second portion of the label that has been adhered to the package and subjected to the sterilization procedure being removed by being torn along a perforation between the first and second portions of the label, FIG. 4*e* also illustrates that the first portion of the label remains attached to the package of the sterilized objects for use in other control procedures; and FIG. 4*f* illustrates the second portion of the label of FIG. 4*e* being adhered to a patient's file after removal of the liner of the second portion exposes the adhesive of the second portion.

DETAILED DESCRIPTION

Figure 1:
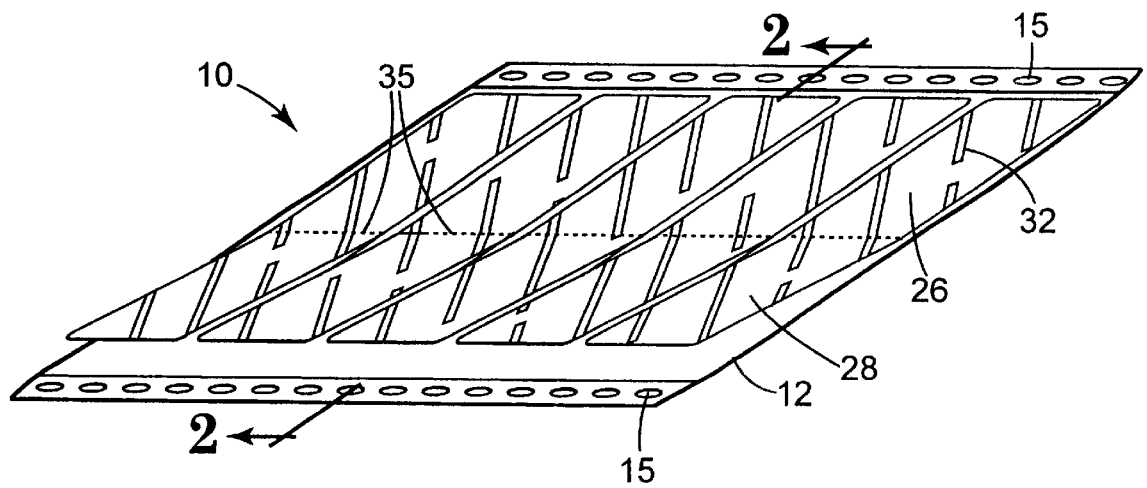
FIG. 1 is a perspective view of a label according to one aspect of the present invention.
Figure 2:
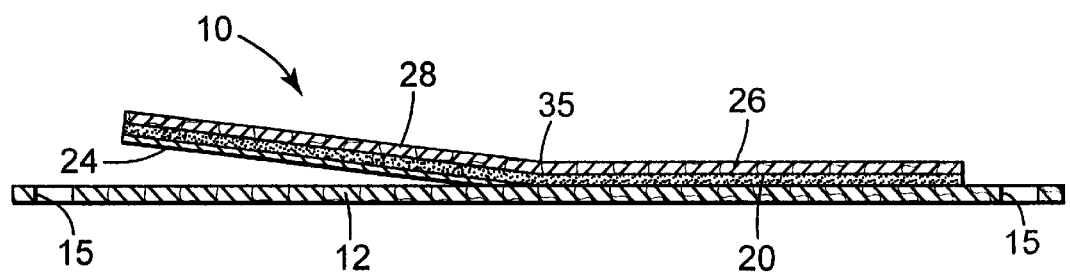
FIG. 2 is a sectional view taken approximately along lines 2—2 of FIG. 1 with the scale of certain elements of label exaggerated in FIG. 2 in order to emphasize details.

Referring now to FIGS. 1 and 2, there is shown a preferred embodiment of label 10 according to the present invention. While the label 10 is preferably used in accordance with a novel sterilization tracking system which is described below, the label 10 may simply be used with objects or goods that are to be subjected to a sterilization procedure. The label 10 has particular utility when used in conjunction with a sterilization procedure which utilizes hydrogen peroxide during at least a portion of the procedure.

The label 10 preferably comprises first 26 and second 28 portions constructed to be manually separable from each other. Preferably, perforations 35 are situated between the first 26 and second 28 portions. While the perforations 35 should afford manual tearing of the second portion 28 from the first portion 26, this portion of the label should withstand the rigors of the sterilization procedure so as not to unduly weaken the attachment between the first and second portions 26 and 28 in order to avoid separation of the first and second portions 26 and 28 during the sterilization procedure.

While the label preferably includes perforations 35, the present invention could alternatively utilize any means for rendering the label tearable between the first and second portions 26 and 28. For example, such a means may comprise a weakened portion provided by scoring, cutting, drilling, stamping, slitting or other partial destruction of the material between the first and second portions 26 and 28, or combinations of such means.

The first and second portions 26 and 28 are preferably substantially the same size and shape. In the depicted embodiment, they form a rectangle.

The first and second portions 26 and 28 may be provided by a backing constructed from a material capable of withstanding the rigors of a sterilization cycle. Examples of suitable materials include paper, polymers, laminates and combinations thereof U.S. Pat. No. 4,898,762 (the entire contents of which are herein expressly incorporated by reference) discloses an isotactic polypropylene backing suitable for use in the present invention. Further non-limiting examples include latex saturated paper backings, foil backings, woven and nonwoven backings, polyolefin-based film backings (e.g. polyethylene), and polyester film backings.

Each of the first 26 and second 28 portions have a first side constructed to receive indicia and/or information provided by an indicating composition or indicating ink. The indicia received on the first and second portions 26 and 28 may be provided by printing, stamping, dipping, manual writing or by automated means such as a computer printer. The printed indicia on the first portion may optionally comprise sterilization equipment identification, sterilization conditions, dates, general comments, validity date, names (e.g. the operator of the sterilizer), or contents of the packaging. The indicia on the second portion may comprise information for the patient's file. For example, the first and second sides may include a surface treatment which assists in retaining an indicating composition. Such a surface treatment may also be used to assist the first and second sides in receiving ink from a permanent ink pen or marker.

The first 26 and second 28 portions preferably each have an adhesive 20 that is on a side opposite the side constructed to receive printed indicia. The adhesive 20 may be any suitable adhesive capable of withstanding the rigors of a sterilization procedure and yet retain a suitable degree of adhesive quality. The adhesive 20 may be a permanent adhesive, a removable adhesive or a repositionable adhesive. Unlike some conventional tracking systems however, the adhesive 20 need not be a removable or repositionable adhesive, but could optionally comprise a permanent adhesive.

Nonlimiting examples of adhesives suitable for use in the present invention include normally tacky, pressure sensitive adhesives known in the art. The adhesives useful herein are resistant to softening upon exposure to sterilization conditions (including heat, steam or other chemical methods such as hydrogen peroxide and ethylene oxide). Typical pressure sensitive adhesives employed with indicator tapes and labels that are also useful in the present invention include water insoluble natural rubber-based adhesives, natural rubber and synthetic rubber blend adhesives, styrene-isoprene-styrene block copolymers with tackifying resins, vinyl ethers, high molecular weight acrylate copolymers having minimal amounts of plasticizing monomers included therein. See e.g., U.S. Pat. Nos. 2,889,799; 3,067,057; 3,078,182; 3,311,084; and 4,188,437 (the entire contents of each of which are herein incorporated by reference).

Nonlimiting examples of adhesives include the water dispersible pressure sensitive adhesives disclosed in U.S. Pat. Nos. 2,838,421; 3,441,430; 3,865,770; 4,413,080 and 4,569,960 (the entire contents of each of which is herein incorporated by reference). Further examples of water-soluble or water-dispersible pressure sensitive adhesive compositions can be found in U.S. Pat. Nos. 3,096,202; 3,152,940; 3,763,117; 3,890,292; 4,341,680; 4,388,432; 4,413,082 and 5,125,995 (the entire contents of each of which is herein incorporated by reference). The adhesive may optionally comprise water dispersible adhesives such as those disclosed in U.S. Pat. Nos. 5,460,880; 5,518,763 and 5,622,764 (the entire contents of which are herein incorporated by reference), especially when the present invention is utilized in a steam sterilization procedure.

Preferably, the adhesive 20 is associated with substantially all of one side of the first and second portions 26 and 28. Alternatively, only parts of the first and second portions 26 and 28 may have an adhesive associated therewith. The adhesive 20 may be applied in various manners such as, for example, coating (e.g. stripe, knife, pattern or flood coating) or printing such as gravure printing.

Preferably the adhesive 20 is a unitary adhesive in that the adhesive associated with the first portion 26 is substantially the same as the adhesive associated with the second portion 28. Optionally the adhesive 20 associated with the first portion 26 may be substantially different than the adhesive associated with the second portion 28. For example, the adhesive associated with the first portion 26 may comprise a repositionable adhesive and the adhesive associated with the second portion 28 may comprise a permanent adhesive. The converse of this example could also be employed.

At least one and preferably both of the first and second portions 26 and 28 have an indicating composition 32 on the same side as the side that is constructed to receive printed indicia. Providing an indicating composition 32 on both the first and second portions 26 and 28 affords the use of the information associated with the indicating composition 32 to both a viewer of the first portion 26 and a viewer of the second portion 28. This is particularly helpful when the first and second portions 26 and 28 are separated.

Indicating compositions suitable for use in the present invention have a first indicating state prior to exposure to a sterilization procedure and a second indicating state after exposure to the sterilization procedure. Suitable indicator compositions are described in U.S. Pat. Nos. 2,118,144; 2,937,279; 3,098,751; 3,258,312; 3,311,084; 3,360,337; 3,360,338; 3,360,339; 3,386,807; 3,523,011; 3,627,469; 3,667,916; 3,684,737; 3,852,034; 3,862,824; 4,138,216; 4,015,937; 4,094,642; 4,168,779; 4,240,926; 4,382,063, 5,064,576; and 5,451,372 (the entire contents of each of which are herein incorporated by reference). UK Patent Nos. 1458533 and 1370470 and EPO Publication No. 0282178 also disclose suitable compositions (the entire contents of each of which are herein incorporated by reference). The literature also describes suitable compositions. See Royce and Bower, "An Indicator Control Device for Ethylene Oxide Sterilization." J. Pharm. and Pharm. 11, Suppl. 294T–298T, and Brewer et al, Journal of Pharmaceutical Sciences, pages 57–59, January 1966.

The present invention is associated with a plurality of sterilization procedures including those procedures which utilize hydrogen peroxide, peracetic acid, oxygen (including singlet oxygen), steam, dry heat, ethylene oxide, formaldehyde, and gamma irradiation as a steriliant or as an element in a step in the procedure, and those sterilization procedures which utilize combinations of such sterilants. The present invention may be utilized with procedures which utilize matter in a variety of states such as liquids, gases, fluids, plasmas and sterilization procedures which utilize combinations of those states.

The present invention is particularly suitable for use in a procedure which utilizes hydrogen peroxide. As used herein, vapor phase, liquid phase and plasma hydrogen peroxide sterilization procedures are all within the broad definition of hydrogen peroxide sterilization procedures. Sterilization procedures which utilize hydrogen peroxide as merely a component during a substantial portion of the procedure are also included within the meaning of a hydrogen peroxide sterilization procedure. U.S. Pat. Nos. 4,169,123; 4,169,124; 4,642,165; 4,643,876, 4,744,951; 4,756,882; 4,943,414; and 5,667,753 all describe hydrogen peroxide sterilization procedures and the entire contents of each of which are herein incorporated by reference.

When the present invention is utilized in a steam sterilization procedure, the preferred indicating composition comprises an ink including a lead carbonate sulfur system in a binder system, gravure printed in lines onto a Kraft paper backing. More preferably, the ink comprises 38% binder, 23% sulfur, 15% lacquer thinner, 23% lead carbonate, and 1% clay (available as BENTONE™ 38 from NL Chemicals of Hightstown, N.J.), which ink is constructed in accordance with the teachings of U.S. Pat. No. 5,460,880 (the entire contents of which are incorporated by reference).

An indicating composition for use in a hydrogen peroxide sterilization procedure (e.g. the procedure provided by the Sterrad® Hydrogen Peroxide Plasma Sterilizers available from Advanced Sterilization Products of Irvine, Calif. U.S.A.) is described in U.S. patent application Ser. No. 08/859,759, filed May 21, 1997, entitled, "STERILIZATION INDICATOR" by Ignacio (the entire contents of which are herein incorporated by reference). For example, such an indicating ink may comprise acid fuchsin.

U.S. Pat. Nos. 5,084,239; 5,115,166; 5,288,460; 5,376,332; 5,413,759; 5,413,760 and 5,472,664 (the entire contents of each of which are herein incorporated by reference) describe plasma peracetic acid sterilization procedures for which the present invention may be employed.

An indicating composition for use in a sterilization process including the use of a peracid vapor such as a plasma sterilization procedure (e.g. the procedure provided by the AbTox® Peracetic Acid Plasma Sterilizers available from AbTox of Mundelein, Ill. U.S.A.) is described in U.S. patent application Ser. No. 09/019,341, filed Feb. 5, 1998, entitled, "STERILIZATION MONITORS" by R. Ignacio and A. Piechowski (the entire contents of which are herein incorporated by reference). For example, such an indicating composition may comprise a colorant susceptible to halogenation. Such an indicating ink may comprise fluorescein and/or phenol red.

Preferably, the first indicating state of the composition is a first color (e.g. purple for a hydrogen peroxide cycle) and the second indicating state of the composition is a second color (e.g. green for the hydrogen peroxide cycle) which is different than the first color. The first state could be a substantially clear or transparent or translucent state, and the second state could be a substantially opaque or colored state. The converse of these states could also be employed.

The indicating composition 32 may be provided in the form of printed stripes as shown in FIG. 1. Alternatively, the indicating composition could be provided in the form of printing or symbols or characters. For example, the indicating composition may be provided in the form of characters, such as, "Steam Sterilized" or "Ethylene Oxide Sterilized", or "Hydrogen Peroxide Sterilized if Green". In the first state, such characters may be substantially transparent or difficult to see for a user. In the second state, such letters could be readily apparent to a user. For example, the characters may change from a light color to a dark, opaque color upon exposure to the particular sterilant.

Optionally, one or both of the first and second portions 26 and 28 may include a first indicating composition having a first indicating state prior to exposure to a first sterilization procedure and a second indicating state after exposure to the first sterilization procedure; and a second indicating composition having a first indicating state prior to exposure to a second sterilization procedure (which is of a different type than said first sterilization procedure), and a second indicating state after exposure to the second sterilization procedure. Preferably, the first indicating composition remains in the first indicating state if exposed to the second sterilization procedure, and the second indicating composition remains in the first indicating state if exposed to the first sterilization procedure. For example, the first sterilization procedure may comprise a hydrogen peroxide sterilization procedure and the second sterilization procedure may comprise a steam sterilization procedure. Such a label could help avoid confusion at a location (e.g. a hospital) where both steam and hydrogen peroxide sterilization procedures exist. It also provides a benefit in that only one label needs to be manufactured for both sterilization procedures.

The label 10 preferably includes a first removable liner 12 adhesively attached to the first portion 26 and a second removable liner 24 adhesively attached to the second portion 28. To contribute to ease of use, the first removable liner 12 is preferably adhered to the adhesive of the first portion 26 and is free of attachment to the second portion. Also preferably, the second removable liner 24 is adhered to the adhesive of the second portion 28 and is free of attachment to the first portion 26.

The first removable liner 12 may optionally be the type which includes holes 15 which afford use of the label 10 with word processing equipment such as computers and printers. Alternatively, the first removable liner 12 may be smaller. For example, the first removable liner 12 could merely just cover the adhesive associated with the first portion 26 leaving just enough area for a grasping tab for removal of the liner. In such an instance, the first adhesive liner 12 could simply be separated from the second adhesive liner 24 by a small cut or slit in the material constructing the liners 12 and 24.

The liners 12 and 24 may be constructed from any suitable material. The second liner 24 should be capable of withstanding the rigors of the particular sterilization procedure. Examples of suitable materials include papers, plastics, polymers, laminates and combinations thereof. For example, the liner could comprise a paper coated with a release substance such as wax or a low adhesion backsize.

EXAMPLE 1

A sample label 10 for use in a steam sterilization procedure according to the present invention may be constructed using the following steps.

A backing for the label may comprise 29 pound basis weight Kraft paper ("M-2383 Smooth Crepe Semi-Bleached Kraft Saturating Paper"; available from Mosinee Paper Corp., Mosinee, Wis.). The Kraft paper could be gravure printed in lines with a sulfur-lead ink system in a binder system. The ink can contain a 38% binder, 23% sulfur, 15% lacquer thinner, 23% lead carbonate and 1% clay ("Bertone-38", NL Chemicals, Highstown, N.J.). The binder system may contain 24% nitrocellulose ethyl alcohol; 3% phenol-formaldehyde resin ("Beckcite™24-102"; BTL Specialty Resins, Toledo, Ohio); 9% tricresyl phosphate; 14% butyl alcohol; 27% xylene and 23% butyl acetate.

An adhesive may be uniformly coated on the side of the backing opposite the ink side. The adhesive may comprise a natural rubber based adhesive.

The ink printed Kraft paper could be strengthened using a vulcanized natural rubber-wood rosin system coated onto the paper. The rubber system may comprise 23% natural rubber (Goodyear Tire and Rubber Co., Akron, Ohio); 6% zinc dioxide ("Type A-140"; New Jersey Zinc. Co., Palmerton, Pa.); 29% wood rosin ("Tenex 36-710"; Reichold Chemicals Inc. Oakbrook, Ill.); 2% calcium lithol pigment (Hercules Inc.); and 37% mineral spirits. The vulcanizer used to crosslink the rubber system could be 40% white mineral oil (Type #31 USP; AMOCO Chemical Corp., Chicago, Ill.); 15% tetramethylthirum disulfide accelerator (RT Vanderbilt Co., Norwalk, Conn.); and 45% orthopentamethylenethiuram sulfads (RT Vanderbilt Co.).

The printed, saturated paper backing could then be treated to decrease moisture penetration with a solution containing 19% butyl alcohol, 0.2% phosphoric acid, 9% urea, 0.8% aqueous ammonia, 31% formaldehyde, 6% isopropyl alcohol, 10% acrylic polymer ("Elvacite 2044"; E. I. dupont Nemours, Wilmington, Delaware); 9% butanol and 15% xylene.

A low adhesion backsize may be used on the side of the backing opposite the adhesive side. Depending on the nature of the adhesive, a urethane based low adhesion backsize may be used. The urethane backsize as described in U.S. Pat. No. 2,532,011 (incorporated by reference) may be used.

The backing may optionally be coated with an adhesive priming agent to increase the bond of the adhesive to the backing. A priming agent such as NEOPRENE™ N 115 (E. I. dupont Nemours, Wilmington, Del.) may be used.

The natural rubber-based pressure sensitive adhesive in a solvent system could be coated on the Kraft paper at 0.68 grams per 154.8 $cm^2$ (24 $in^2$) using a standard laboratory knife coater, with drying for about 15 minutes in a forced air oven at 100° C.

The above described assembly may be cut to a dimension of 109 mm×300 m. Paper or other liner material may be cut or slit to dimensions of 45 mm×500 m and 125 mm×500 m. On a rotation machine, the 45 mm slitted liner may be laminated onto the adhesive side of the 109 mm assembly. Next, the 125 mm liner is then laminated on (the now ½ adhesive side of) the previously described 109 mm/45 mm liner assembly. Finally, in the same step, die cut the previously described assembly to dimensions of 102 mm×34 mm including perforations in the middle of the label as a "kiss cut", and at the same time, die-cut the edge holes (e.g. 15 in the drawings) in the liner. In this example, the same tool is die cutting the shape of 102 mm×34 mm, the perforations and the edge holes 15.

EXAMPLE 2

A sample label for use in a hydrogen peroxide sterilization procedure according to the present invention may be constructed using the following steps.

A backing may be constructed using a premium C1S white litho stock with high internal strength and uniform flat finish. The caliper may be 0.0036 inches plus or minus 10% with a basis weight of 60 pounds per ream plus or minus 10 percent. The adhesive may comprise a uniformly coated general purpose ultra permanent type pressure sensitive adhesive with high initial tack. The caliper may be about 0.0006 inches plus or minus 10%. The release liner may comprise a forty pound Fastrip, bleached sulfate stock with a basis weight of 42 pounds per ream plus or minus 10%. The caliper can be about 0.0025 inches thick plus or minus 10%. The liner may have a width of about 13/16 inches.

Unlike example 1, the indicating ink may comprise an indicating composition as described in U.S. patent application Ser. No. 08/859,759, filed May 21, 1997. The particular indicating ink applied to the backing may comprise acid fuchsin. That ink may be used to indicate whether a label has undergone the procedure provided by a Sterrad® Hydrogen Peroxide Plasma Sterilizer. The Sterrad sterilizer is a hydrogen peroxide procedure that utilizes a plasma step.

The thickness of the label may be about 0.0067 inches plus or minus 10%. The width may be about 4 inches plus or minus 1/16 inches. The labels may be placed on the liner at intervals of about 0.118 inches inset about 1/16 inch from the edge of the liner. The bleached sulfate stock of the release liner may have a weight of about 37–47 pounds per ream. The tensile yield strength of the assembly in the machine direction may be 32 pounds per inch width minimum.

The labels may be wound on a three inch core with approximately 2500 feet per roll.

EXAMPLE 3

A sample label for use in a peracid sterilization procedure according to the present invention may be constructed using the following steps.

A label utilizing the same backing, liner and adhesive as Example 2 may be provided. Unlike Example 2, the indicating ink may comprise an indicating composition described in U.S. patent application Ser. No. 09/019,341, filed Feb. 5, 1998, entitled, "STERILIZATION MONITORS" by R. Ignacio and A. Piechowski. The indicating composition comprises a colorant susceptible to halogenation. Such an indicating ink may comprise fluorescein or phenol red.

Figure 3:
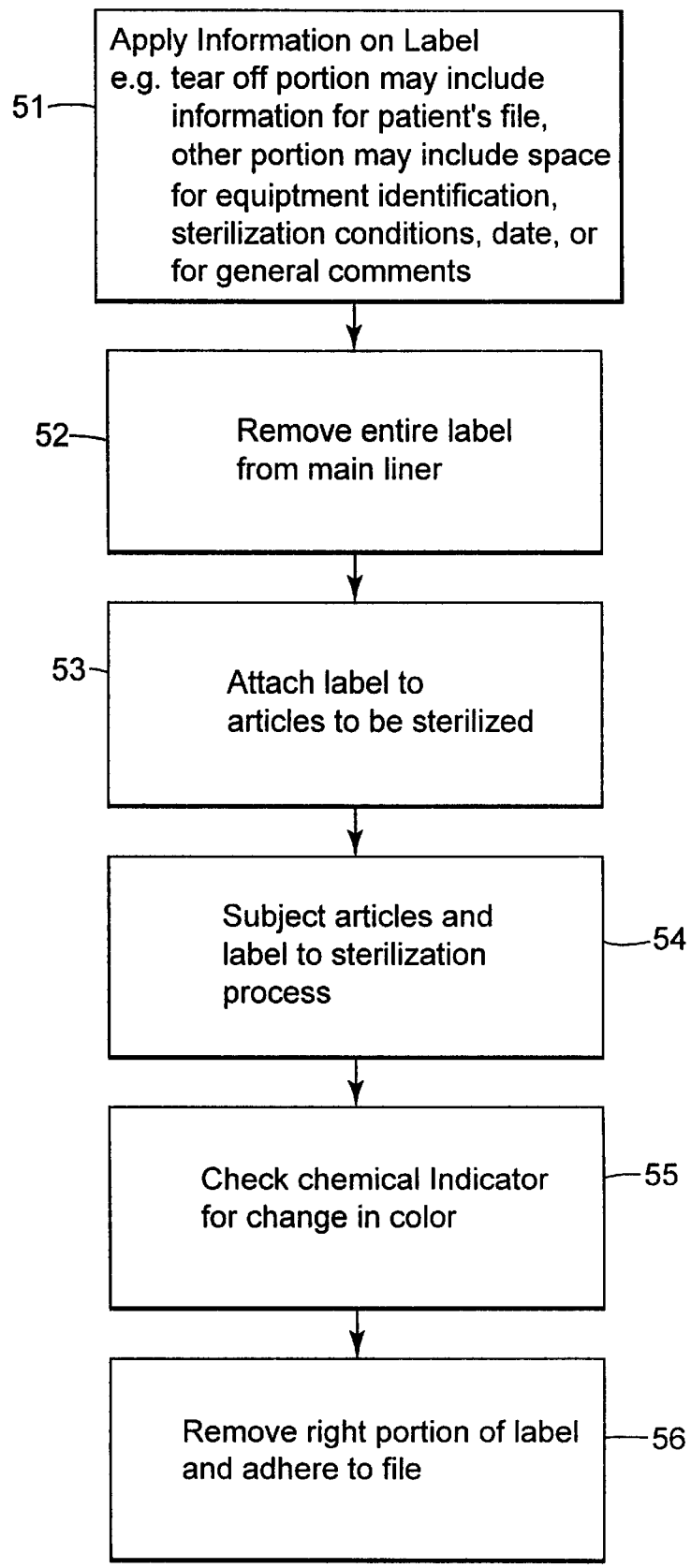
FIG. 3 is a flowchart of one example of the use of the label of FIG. 1 as a component of a sterilization tracking system.
Figure 4C:
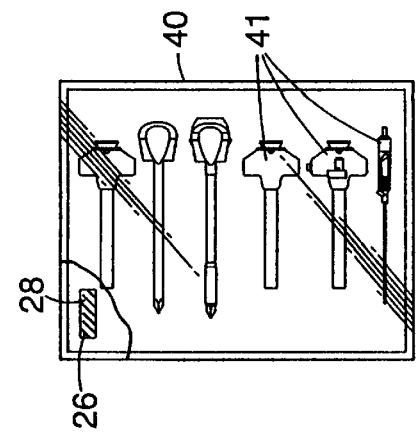
Figure 4F:
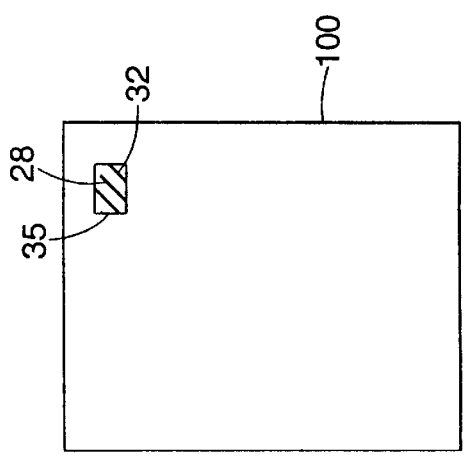
Figure 4B:
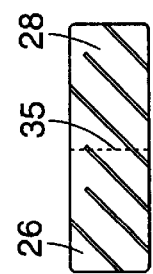
Figure 4E:
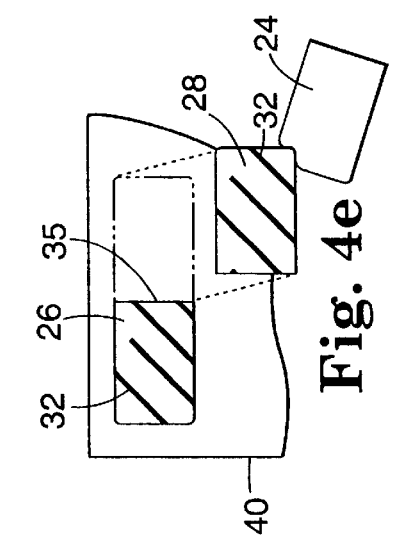
Figure 4A:
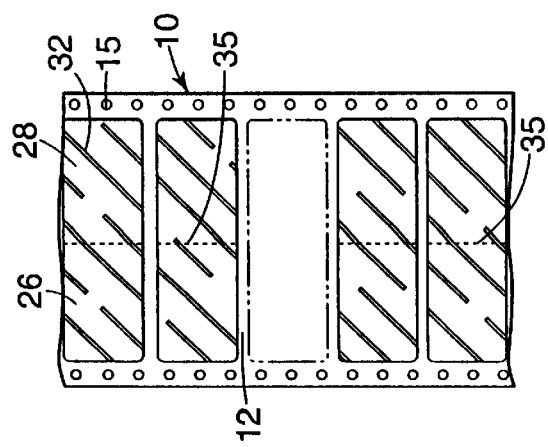
Figure 4D:
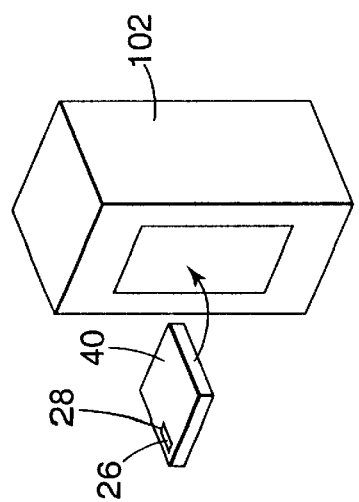

Referring now to FIGS. 3 and 4a through 4f, there is shown a preferred sterilization tracking system which may utilize a novel label 10. The novel method of tracking objects to be sterilized comprises the steps of:

(a) providing a label 10 comprising first 26 and second 28 portions having an adhesive 20, the first 26 and second 28 portions being constructed to be separable from one another; both the first and second portions being suitable for receiving printed information (see step 51, FIG. 3) and both the first and second portions having a composition 32 that changes indicating state when exposed to a sterilization procedure;

(b) adhering the label to packaging of the objects to be sterilized (see steps 52 and 53, FIG. 3; FIGS. 4a, 4b and 4c);

(c) subjecting the objects to be sterilized and the packaging to a sterilization procedure (see step 54, FIG. 3; FIG. 4d);

(d) then removing the second portion of the label from the first portion leaving the first portion adhered to the packaging of the objects (see FIG. 4e); and (e) then adhering the second portion to a patient's file (see step 56 in FIG. 3 and FIG. 4f).

The indicator composition 32 may be checked for a change in color (e.g. step 55) at any point, but it is particularly interesting to check after the objects (and label 10) emerge from the sterilizer.

Preferably, the step of adhering the first portion 26 to the packaging of the objects to be sterilized comprises adhering the first portion 26 to the packaging of the objects to be sterilized with substantially all of the adhesive of the first portion This step contributes to a secure attachment of the label 10 to the packaging of the objects to be sterilized, as opposed to an attachment which may require additional tape to secure the label to the packaging of the objects to be sterilized. The label 10 is preferably free of any attachment means to the packaging 40 except the attachment provided by the adhesive(s) of the label 10 itself. This feature eliminates the need for an additional step during the use of the label 10. In particular, a user need not use separate and distinct tape to attach the label to the packaging 40.

Referring to FIGS. 4a through 4f, a preferred use of the label 10 is shown. The label is particularly suitable for use in the central sterilization supply departments of hospitals. The label 10 can help provide a link between objects that have undergone sterilization and the patient's file. Objects used on a particular patient during a surgical procedure may be traced back from the patient to a sterilizer or load number. The label provides a link between a patient and the various files kept on sterilization parameters in the central sterilization supply department of the hospital.

Preferably, the label 10 is provided with a major liner 12 in the form of a sheet with computer compatible holes 15. In that manner, the various steps of providing indicia to the label 10 may be optionally automated.

The label 10 is removed from the liner 12 (see FIG. 4b), and then subsequently adhered to the package 40 of the objects to be sterilized 41 (See FIG. 4c). When the label 10 is removed from the liner 12, only the adhesive associated with the first portion 26 is exposed as the liner 24 protects the adhesive associated with the second portion 28. When the first portion 26 is adhered to the package 40, preferably substantially all of the adhesive associated with the first portion 26 adheres the label 10 to the package 40 in order to contribute to a secure attachment suitable for withstanding the rigors of a sterilization procedure, even a sterilization procedure which utilizes a vacuum.

The objects to be sterilized 41 may comprise any object that may be subjected to a sterilization procedure such as, but not limited to, disposable or reusable surgical instruments, or goods used in the hospital or laundry.

FIG. 4d illustrates the package 40 (with the label adhered thereto) being placed within a sterilizer 102. Once the sterilization procedure is complete, the label 10 and package 40 are removed from the sterilizer 102. If the sterilizer functions properly, the indicating composition 32 changes state (e.g. color) from its first state to its second state during the sterilization procedure.

The second portion 28 may next be separated from the first portion 26. The first portion 26 remains attached to the packaging 40 and thus may be used in other control procedures (e.g. further documentation) or it may be discarded with the packaging.

The liner 24 remains attached to the second portion 28 during the sterilization procedure thereby affording the adhesive associated with the second portion 28 a degree of protection from the sterilization procedure. After the liner 24 is removed, the second portion 28 may be adhered to the patient's file 100.

The present invention has now been described with reference to several embodiments and examples thereof. It will be apparent to those skilled in the art that many changes or additions can be made in the embodiments described without departing from the scope of the present invention. Thus, the scope of the present invention should not be limited to the structures described in this application, but only by structures described by the language of the claims and the equivalents of those structures.

What is claimed is:

1. A label for use in a tracking system for tracking objects to be subjected to a hydrogen peroxide sterilization procedure, the label comprising:

(a) first and second portions constructed to be manually separable from each other, each of said first and second portions having a first side constructed to receive printed indicia, and a second side with an adhesive, (b) the first side of each of said first and second portions including an indicating composition with a first indicating state prior to exposure to the hydrogen peroxide sterilization procedure and a second indicating state after exposure to the hydrogen peroxide sterilization procedure, and (c) a removable liner adhered to the adhesive.

2. A label according to claim 1 wherein perforations are situated between the first and second portions.

3. A label according to claim 1 wherein the label includes a first removable liner attached to the first portion and a second removable liner attached to the second portion.

4. A label according to claim 1 wherein the first indicating state is a first color and the second indicating states is a second color which is different than the first color.

5. A label for use in a tracking system for tracking objects to be subjected to a hydrogen peroxide sterilization procedure, the label comprising:

(a) first and second portions with perforations situated between the first and second portions affording separation of the first and second portions from each other, each of said first and second portions having a first side constructed to receive printed indicia, and a second side with an adhesive, (b) the first side of said first and second portions including an indicating composition with a first indicating state prior to exposure to the hydrogen peroxide sterilization procedure and a second indicating state after exposure to the hydrogen peroxide sterilization procedure, and (c) a liner adhered to the adhesive.

6. A label according to claim 5 wherein the label includes a first removable liner attached to the first portion and a second removable liner attached to the second portion.

7. A label according to claim 5 wherein the first indicating state is a first color and the second indicating states is a second color which is different than the first color.

8. A label for use in a tracking system for tracking objects to be subjected to a sterilization procedure, the label comprising:

(a) first and second portions constructed to be manually separable from each other, each of said first and second portions having a first side constructed to receive printed indicia, and a second side with an adhesive, (b) the first side of at least one of said first and second portions including an indicating composition with a first indicating state prior to exposure to the sterilization procedure and a second indicating state after exposure to the sterilization procedure, and (c) a first removable liner adhered to the adhesive of the first portion and free of attachment to the second portion, and a second removable liner adhered to the adhesive of the second portion and free of attachment to the first portion.

9. A label according to claim 8 wherein perforations are situated between the first and second portions.

10. A label according to claim 8 wherein both the first and second portions have the indicating composition.

11. A label according to claim 8 wherein the first indicating state is a first color and the second indicating states is a second color which is different than the first color.

12. A method of tracking objects to be sterilized by a hydrogen peroxide sterilization procedure, the method comprising the steps of:

(a) providing a label comprising first and second portions having an adhesive, the first and second portions being constructed to be separable from one another; both the first and second portions being suitable for receiving printed information, and both the first and second portions having a composition that changes indicating state when exposed to a hydrogen peroxide sterilization procedure;

(b) adhering the label to packaging of objects to be sterilized;

(c) subjecting the packaging and the objects to be sterilized to a hydrogen peroxide sterilization procedure;

(d) then removing the second portion of the label from the first portion leaving the first portion adhered to the packaging of the objects to be sterilized; and (e) then adhering the second portion to a patient's file.

13. A method according to claim 12 wherein the step of adhering the first portion to the packaging of the objects to be sterilized comprises adhering the first portion to the packaging of the objects to be sterilized with substantially all of the adhesive of the first portion.

* * * * *